United States Patent
Han et al.

(10) Patent No.: US 11,865,522 B2
(45) Date of Patent: Jan. 9, 2024

(54) METHOD FOR PREPARING ZINC FERRITE-BASED CATALYST AND ZINC FERRITE-BASED CATALYST PREPARED THEREBY

(71) Applicant: LG CHEM, LTD., Seoul (KR)

(72) Inventors: Sang Jin Han, Daejeon (KR); Dong Hyun Ko, Daejeon (KR); Kyong Yong Cha, Daejeon (KR); Ye Seul Hwang, Daejeon (KR); Sunhwan Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 21 days.

(21) Appl. No.: 17/293,586

(22) PCT Filed: Jul. 13, 2020

(86) PCT No.: PCT/KR2020/009188
§ 371 (c)(1),
(2) Date: May 13, 2021

(87) PCT Pub. No.: WO2021/060681
PCT Pub. Date: Apr. 1, 2021

(65) Prior Publication Data
US 2022/0008899 A1    Jan. 13, 2022

(30) Foreign Application Priority Data
Sep. 27, 2019  (KR) ........................ 10-2019-0119627

(51) Int. Cl.
*B01J 23/80* (2006.01)
*B01J 23/00* (2006.01)
(Continued)

(52) U.S. Cl.
CPC ............ *B01J 23/80* (2013.01); *B01J 23/005* (2013.01); *B01J 37/009* (2013.01);
(Continued)

(58) Field of Classification Search
None
See application file for complete search history.

(56) References Cited

U.S. PATENT DOCUMENTS 7,879,153 B1   2/2011  Seo et al.
2010/0121123 A1  5/2010  Chung et al.
(Continued)

FOREIGN PATENT DOCUMENTS

CN    110198783 A    9/2019
EP    3292910 A1    3/2018
(Continued)

OTHER PUBLICATIONS

Machine translation JP 2015-167886. Accessed Jun. 1, 2022 (Year: 2022).*
(Continued)

*Primary Examiner* — Coris Fung
*Assistant Examiner* — Keling Zhang
(74) *Attorney, Agent, or Firm* — Bryan Cave Leighton Paisner LLP

(57) ABSTRACT

A method for preparing a zinc ferrite-based catalyst comprising: obtaining a precipitate by bringing a metal precursor solution including a zinc precursor, a ferrite precursor, a solution containing an acid and water into contact with a basic aqueous solution; filtering the precipitate; drying the filtered precipitate; and firing the dried precipitate, wherein the solution containing the acid includes one or more of nitric acid ($HNO_3$) and hydrocarbon acid.

8 Claims, 5 Drawing Sheets

(51) Int. Cl.

| | |
|---|---|
| *B01J 37/00* | (2006.01) |
| *B01J 37/02* | (2006.01) |
| *B01J 37/03* | (2006.01) |
| *B01J 37/06* | (2006.01) |
| *B01J 37/08* | (2006.01) |
| *C07C 5/48* | (2006.01) |

(52) U.S. Cl.
CPC ......... *B01J 37/0236* (2013.01); *B01J 37/031* (2013.01); *B01J 37/06* (2013.01); *B01J 37/08* (2013.01); *C07C 5/48* (2013.01); *C07C 2523/80* (2013.01)

(56) References Cited

U.S. PATENT DOCUMENTS

| | | |
|---|---|---|
| 2011/0004041 A1 | 1/2011 | Chung et al. |
| 2012/0059208 A1 | 3/2012 | Mamedov et al. |
| 2013/0209351 A1 | 8/2013 | Shin et al. |
| 2013/0217568 A1* | 8/2013 | Hazin .................... B01J 23/002 502/226 |
| 2018/0207621 A1 | 7/2018 | Han et al. |
| 2020/0001279 A1* | 1/2020 | Han .................... B01J 37/08 |

FOREIGN PATENT DOCUMENTS

| | | | |
|---|---|---|---|
| JP | H06-060020 | | 8/1994 |
| JP | 2005-144374 | | 6/2005 |
| JP | 2015-167886 | | 9/2015 |
| JP | 2015167886 A | * | 9/2015 |
| KR | 10-0847206 | | 7/2008 |
| KR | 10-2009-0034139 | | 4/2009 |
| KR | 10-2011-0098513 | | 9/2011 |
| KR | 10-1071230 | | 10/2011 |
| KR | 10-1472230 | | 12/2014 |
| KR | 10-1508776 | | 4/2015 |
| KR | 10-2017-0108843 | | 9/2017 |
| KR | 10-2019-0077975 | | 7/2019 |
| KR | 20190077975 | * | 7/2019 |
| WO | 2009-045002 | | 4/2009 |
| WO | WO-2018080025 A1 | * | 5/2018 .............. B01J 21/02 |

OTHER PUBLICATIONS

Machine translation of JP 2015167886A (Year: 2015).*
Machine translation of WO2018080025A1 (Year: 2018).*
Office Action of Korean Patent Office in Appl'n No. 10-2020-0086254, dated Oct. 25, 2022.
Ladole, "Preparation and Characterization of Spinel Zinc Ferrite $ZnFe_2O_4$," International Journal of Chemical Sciences 10(3):1230-1234 (2012).

\* cited by examiner

[Figure 1]
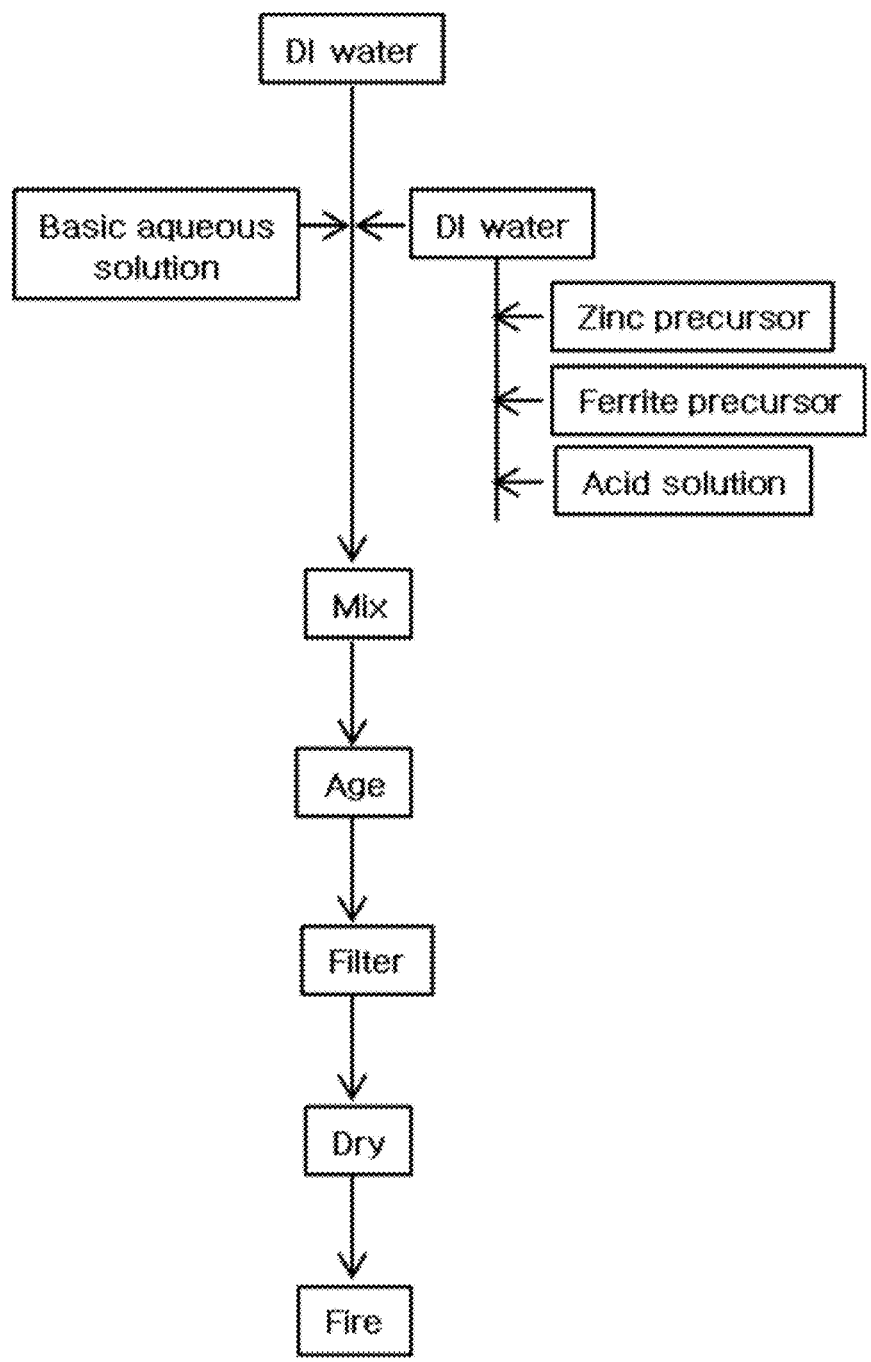

[Figure 2]
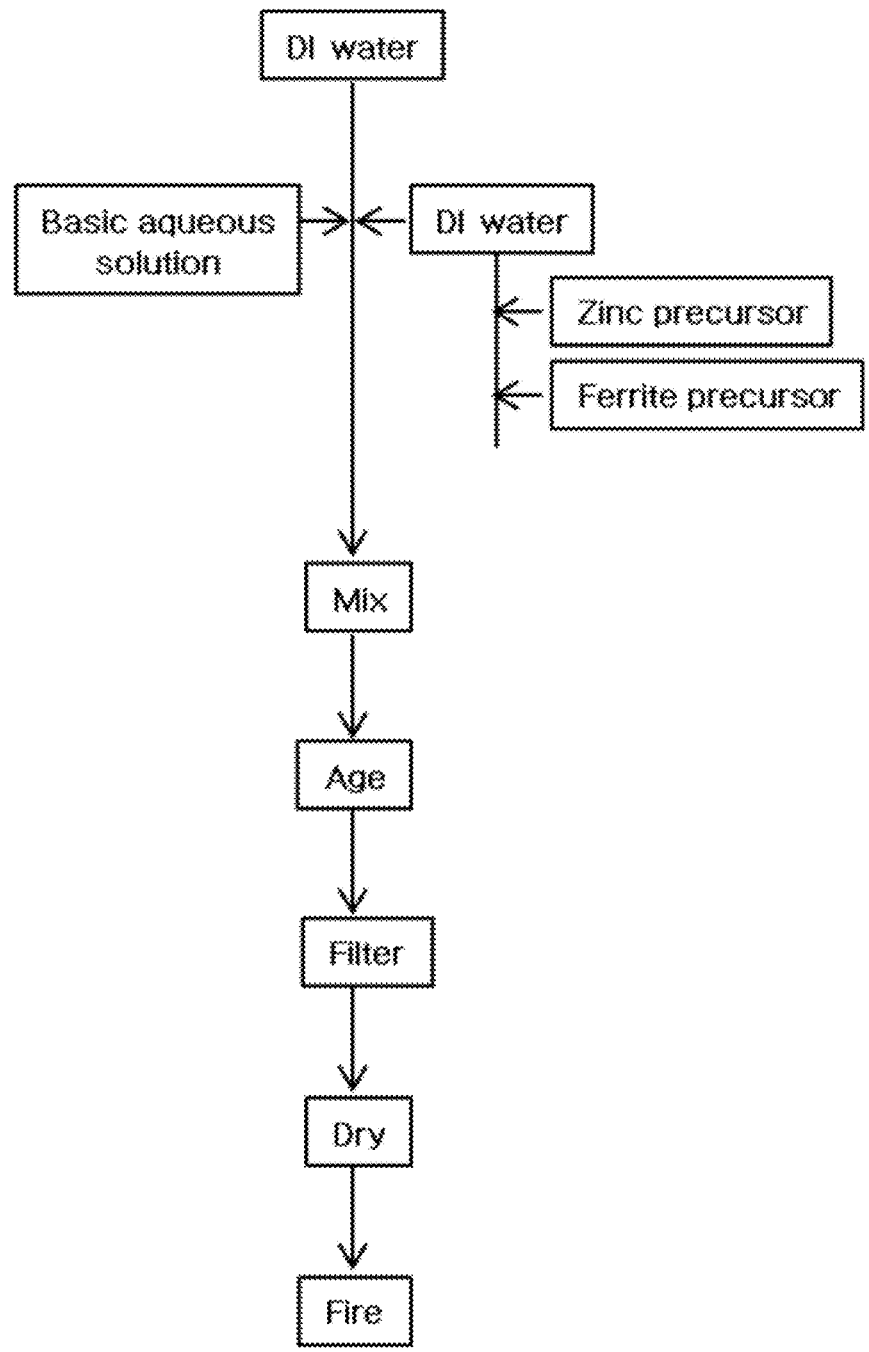

[Figure 3]
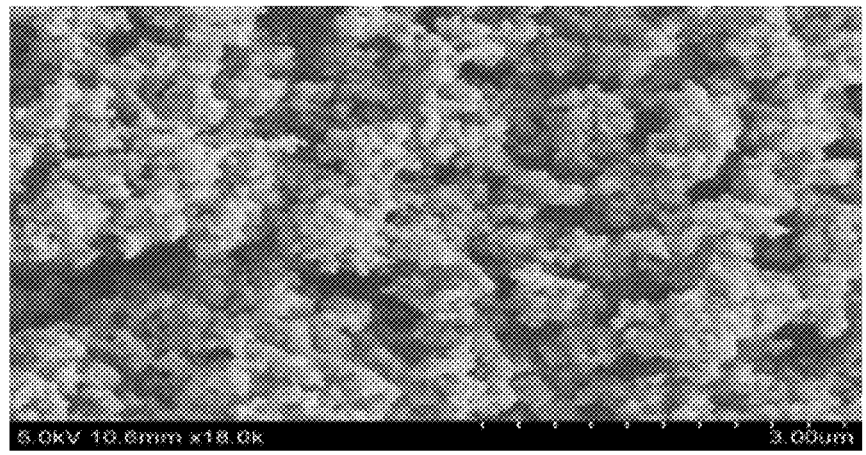
[Figure 4]
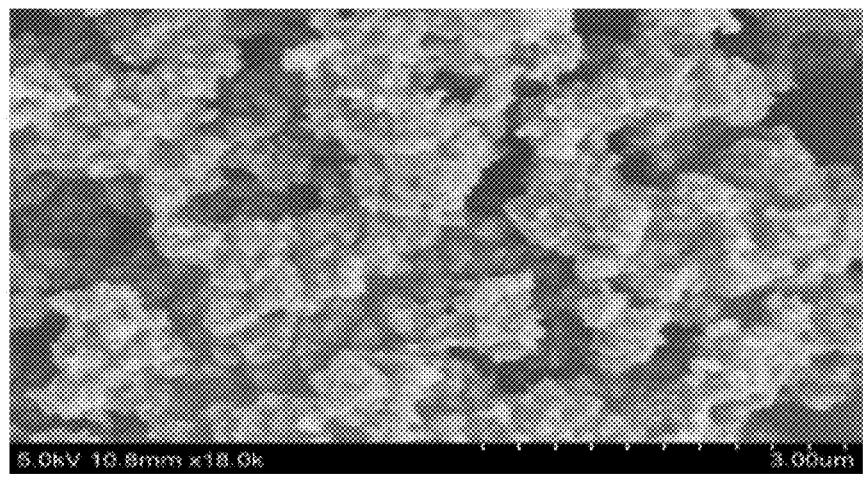
[Figure 5]
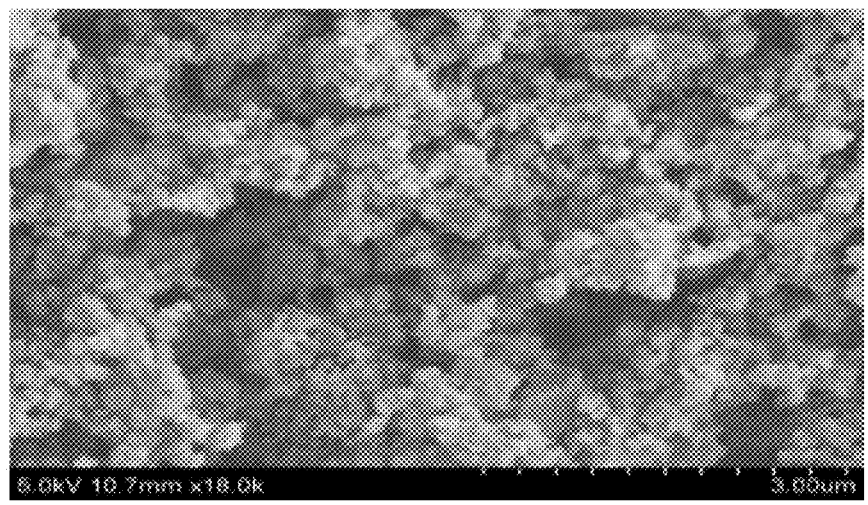

[Figure 6]
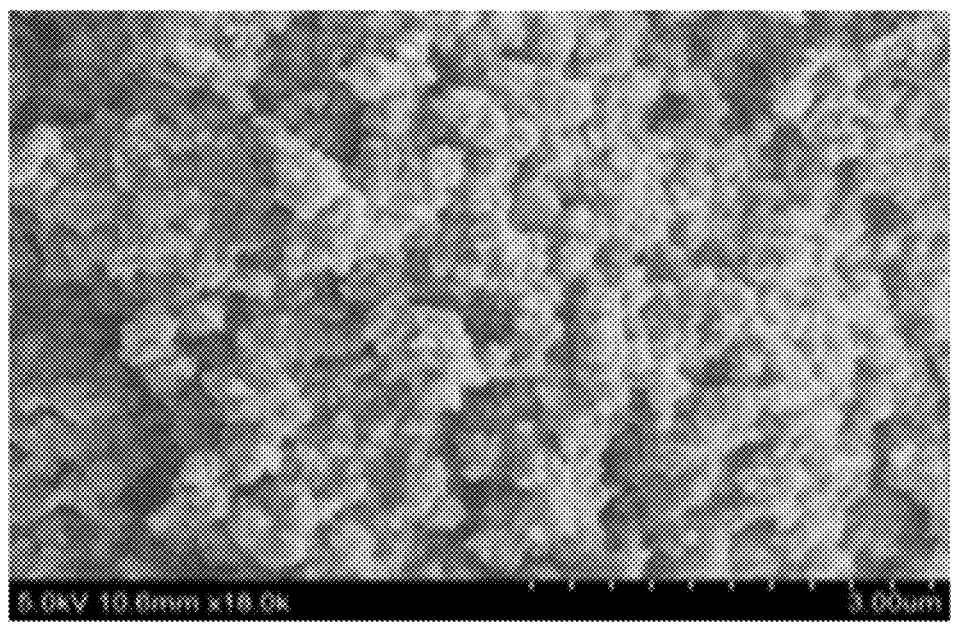
[Figure 7]
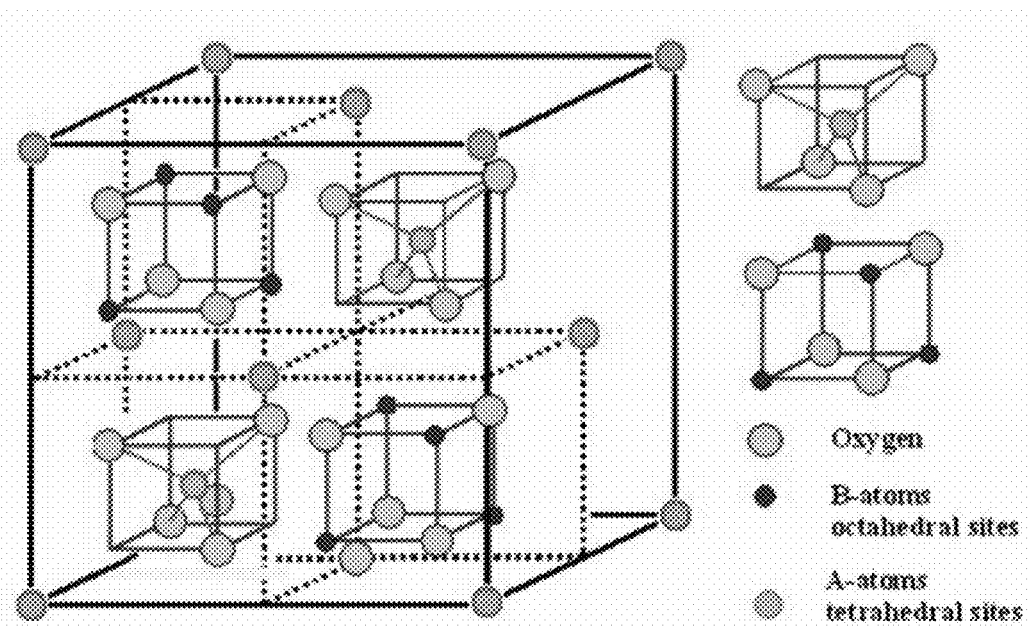
$AB_2O_4$ spinel The red cubes are also contained in the back half of the unit cell

[Figure 8]
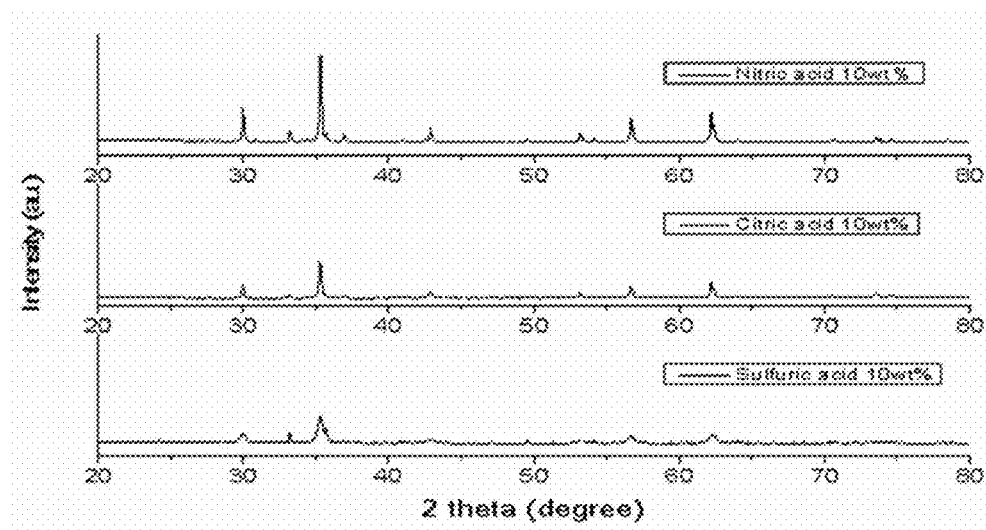

METHOD FOR PREPARING ZINC FERRITE-BASED CATALYST AND ZINC FERRITE-BASED CATALYST PREPARED THEREBY

CROSS-REFERENCE TO RELATED APPLICATION(S)

This application is a National Stage Application of International Application No. PCT/KR2020/009188 filed on Jul. 13, 2020, which claims priority to and the benefit of Korean Patent Application No. 10-2019-0119627 filed in the Korean Intellectual Property Office on Sep. 27, 2019, the entire contents of which are incorporated herein by reference.

TECHNICAL FIELD

The present application relates to a method for preparing a zinc ferrite-based catalyst and a zinc ferrite-based catalyst prepared thereby.

BACKGROUND 1,3-butadiene is an intermediate of petroleum chemical products, and demands for 1,3-butadiene and the value thereof are gradually increasing globally. The 1,3-butadiene has been prepared by using naphtha cracking, the direct dehydrogenation reaction of butene, the oxidative dehydrogenation reaction of butene, and the like.

However, since the naphtha cracking process consumes a lot of energy due to high reaction temperature and is not a single process for producing only 1,3-butadiene, there is a problem in that other fundamental fractions in addition to 1,3-butadiene are produced in excess. Further, the direct dehydrogenation reaction of n-butene is thermodynamically adverse and requires high temperature and low pressure conditions for producing 1,3-butadiene with high yield as an endothermic reaction, and thus is not suitable as a commercialization process for producing 1,3-butadiene.

Meanwhile, the oxidative dehydrogenation reaction of butene is a reaction in which butene and oxygen react with each other in the presence of a metal oxide catalyst to produce 1,3-butadiene and water, and has a very thermodynamically favorable advantage because stable water is produced. Further, since the oxidative dehydrogenation reaction of butene is an exothermic reaction unlike the direct dehydrogenation reaction of butene, 1,3-butadiene with high yield can be obtained even at lower reaction temperature than the direct dehydrogenation reaction, and the oxidative dehydrogenation reaction of butene can become an effective single production process capable of satisfying the demands for 1,3-butadiene because an additional heat supply is not required.

The metal oxide catalyst is generally synthesized by a precipitation method, and since the one-time amount of metal oxide catalyst produced is small due to technical and spatial limitations, the catalyst is prepared by repeating the same process several times in order to satisfy a target amount. The catalysts thus prepared over several times can have different reactivity with the reactant depending on the preparation order, and such a difference in reactivity among the catalysts is directly related to the yield of the product (butadiene), so that studies to reduce the difference in reactivity among the catalysts have been continuously carried out.

BRIEF DESCRIPTION

Technical Problem

The present application has been made in an effort to provide a method for preparing a zinc ferrite-based catalyst and a zinc ferrite-based catalyst prepared thereby.

Technical Solution

An exemplary embodiment of the present application provides a method for preparing a zinc ferrite-based catalyst, the method comprising:

obtaining a precipitate by bringing a metal precursor solution comprising a zinc precursor, a ferrite precursor, a solution containing an acid, and water into contact with a basic aqueous solution; and filtering the precipitate, and then drying the filtered precipitate, and firing the dried precipitate, in which the solution containing the acid comprises one or more of nitric acid ($HNO_3$) and hydrocarbon acid.

Further, another exemplary embodiment of the present application provides a zinc ferrite-based catalyst prepared by the method for preparing a zinc ferrite-based catalyst.

In addition, still another exemplary embodiment of the present application provides a method for producing butadiene, the method comprising:

preparing the zinc ferrite-based catalyst; and producing butadiene by using the zinc ferrite-based catalyst in an oxidative dehydrogenation reaction of butene.

The present invention provides a method for preparing butadiene.

Advantageous Effects

A zinc ferrite-based catalyst according to an exemplary embodiment of the present application can increase the size of the crystal structure of the zinc ferrite-based catalyst by introducing a solution containing an acid, such as nitric acid and/or hydrocarbon acid, into a co-precipitation step during the process of preparing the zinc ferrite-based catalyst, and accordingly, can increase the activity of the catalyst.

Further, since the zinc ferrite-based catalyst according to an exemplary embodiment of the present application can reduce impurities $Cl^-$ ions which can be present in the catalyst, it is possible to prevent the corrosion of preparation process equipment.

Therefore, the zinc ferrite-based catalyst according to an exemplary embodiment of the present application can obtain a higher yield of 1,3-butadiene than a zinc ferrite-based catalyst in the related art, which is used for oxidative dehydrogenation of butene.

BRIEF DESCRIPTION OF DRAWINGS

FIG. 1 is a process diagram for performing a method for preparing a zinc ferrite-based catalyst according to an exemplary embodiment of the present application.

FIG. 2 is a process diagram for performing a method for preparing a zinc ferrite-based catalyst according to the co-precipitation method in the related art.

FIG. 3 is a SEM photograph of a zinc ferrite-based catalyst according to Example 1 of the present application.

FIG. 4 is an SEM photograph of a zinc ferrite-based catalyst according to Example 2 of the present application.

FIG. 5 is an SEM photograph of a zinc ferrite-based catalyst according to Example 3 of the present application.

FIG. 6 is an SEM photograph of a zinc ferrite-based catalyst according to Comparative Example 1 of the present application.

FIG. 7 is a view schematically illustrating the lattice structure of a zinc ferrite-based catalyst according to an exemplary embodiment of the present application.

FIG. 8 is a result of performing XRD analysis on zinc ferrite-based catalysts according to Examples 3 and 4 of the present application and Comparative Example 2.

DETAILED DESCRIPTION

Hereinafter, preferred exemplary embodiments of the present application will be described. However, the exemplary embodiments of the present application can be modified into various other forms, and the scope of the present application is not limited to the exemplary embodiments which will be described below. Further, the exemplary embodiments of the present application are provided to explain the present invention in more detail to a person with ordinary skill in the art.

In the present specification, the "yield (%)" is defined as a value obtained by dividing the number of moles of 1,3-butadiene, which is a product of an oxidative dehydrogenation reaction, by the number of moles of butene which is a raw material. For example, the yield can be represented by the following equation.

Yield (%)=[(the number of moles of 1,3-butadiene produced)/(the number of moles of butene supplied)]×100

In the present specification, the "conversion (%)" refers to a rate at which a reactant is converted into a product, and for example, the conversion of butene can be defined by the following equation.

Conversion (%)=[(the number of moles of butene reacted)/(the number of moles of butene supplied)]×100

In the present specification, the "selectivity (%)" is defined as a value obtained by dividing the change amount of butadiene (BD) by the change amount of butene (BE). For example, the selectivity can be represented by the following equation.

Selectivity (%)=[(the number of moles of 1,3-butadiene or COx produced)/(the number of moles of butene reacted)]×100

In the specification, the "butadiene" means 1,3-butadiene.

As described above, a ferrite-based catalyst is generally used for the production of butadiene by an oxidative dehydrogenation reaction of butene, and the ferrite-based catalyst was synthesized by using a co-precipitation method.

In general, the activity of the ferrite-based catalyst synthesized by a co-precipitation method is affected by the size of the crystal structure. Further, $Cl^-$ ions are present as impurities in the ferrite-based catalyst, and the $Cl^-$ ions are one of the elements which cause corrosion of synthesis equipment and reaction equipment. Some of the impurities can be removed in a washing step after the co-precipitation step, but are not removed below a certain level.

Thus, the present inventors have conducted studies on a method which can increase the activity of a ferrite-based catalyst by adjusting the size of crystal size in the ferrite-based catalyst and can decrease $Cl^-$ ions in the ferrite-based catalyst, and completed the present invention.

A method for preparing a zinc ferrite-based catalyst according to an exemplary embodiment of the present application comprises: obtaining a precipitate by bringing a metal precursor solution comprising a zinc precursor, a ferrite precursor, a solution containing an acid, and water into contact with a basic aqueous solution; and filtering the precipitate, and then drying the filtered precipitate, and firing the dried precipitate, in which the solution containing the acid comprises one or more of nitric acid ($HNO_3$); and hydrocarbon acid.

It is known that the activity of a ferrite-based catalyst having a spinel structure ($AFe_2O_4$) is good as a catalyst for a process of producing 1,3-butadiene through the oxidative dehydrogenation reaction of butene.

Meanwhile, it is known that a ferrite-based catalyst exhibits a result that is better than a bismuth-molybdenum catalyst (Mo—Bi catalyst) in terms of reactivity with 2-butene, particularly, trans-2-butene. Accordingly, even though the Mo—Bi catalyst is applied to the oxidative dehydrogenation reaction of 2-butene, an effect which is the same as that in the present invention, that is, a result such as the conversion rate of butene or selectivity of butadiene is not obtained.

In this case, a $ZnFe_2O_4$ catalyst used in the oxidative dehydrogenation reaction of butene is generally produced by a co-precipitation method. In the co-precipitation, the $ZnFe_2O_4$ catalyst is prepared by subjecting the raw materials to precipitation, stirring, aging, washing, drying, and firing processes, and a step in which zinc (Zn) and ferrite (Fe) are homogeneously precipitated is very important.

There is a problem in that in the process of synthesizing a zinc ferrite catalyst using the co-precipitation method in the related art, an $\alpha$-$Fe_2O_3$ phase is formed. The $\alpha$-$Fe_2O_3$ phase exhibits a low butadiene selectivity in the oxidative dehydrogenation reaction of butene, whereas the $ZnFe_2O_4$ phase exhibits a high butadiene selectivity.

Accordingly, the present inventors have conducted studies on a synthesis method capable of controlling the production of the $\alpha$-$Fe_2O_3$ phase in order to improve the selectivity of butadiene, so that when a zinc ferrite-based catalyst is prepared by introducing a solution comprising one or more of nitric acid ($HNO_3$) and hydrocarbon acid in the co-precipitation step of the process of synthesizing a zinc ferrite-based catalyst using the existing co-precipitation method, the $\alpha$-$Fe_2O_3$ phase is decreased and the size of the crystal structure is increased, and as a result, the activity of the catalyst is increased. Ultimately, it was revealed that in the oxidative dehydrogenation reaction of butene, a high yield of 1,3-butadiene could be obtained by increasing the selectivity of butadiene.

In an exemplary embodiment of the present application, a solution comprising one or more of nitric acid ($HNO_3$) and hydrocarbon acid is bonded to $Cl^-$ ions present in a zinc precursor and a ferrite precursor by introducing the solution comprising one or more of nitric acid ($HNO_3$); and hydrocarbon acid in the co-precipitation step of the process of synthesizing a zinc ferrite-based catalyst, and accordingly, it is possible to decrease $Cl^-$ ions which can be present as impurities in the zinc ferrite-based catalyst.

The lattice structure of a zinc ferrite-based catalyst according to an exemplary embodiment of the present application is schematically illustrated in the following FIG. 7. As in the following FIG. 7, the crystal structure of $ZnFe_2O_4$ which is a zinc ferrite-based catalyst, has an octahedral B lattice (B site) and a tetrahedral A lattice (A site) which are alternately repeated. The A site is composed of 24 metal ions comprising 8 metal ions and 16 metal ions and 32 oxygen ions, and A lattice and B lattice are opposite to each other in the direction of the magnetic moment. Since transition metal ions having unpaired electrons in the 3d electron orbital have different spin magnetic moments depending on the number of these electrons, the magnetism varies depending on whether the metal ion selectively enters either the A lattice or the B lattice. Fe' ions enter the octahedral B lattice and $Zn^{2+}$ ions enter the A lattice. That is, when impurities comprising $Cl^-$ and the like are reduced in a co-precipitation solution, Zn' and Fe' help to form a crystal structure, so that the $\alpha$-$Fe_2O_3$ crystal structure can be reduced.

In addition, when the particle size in a slurry state is small in the co-precipitation step, the crystal size after firing tends to increase. Accordingly, in the co-precipitation step, $Cl^-$ ions and the like are removed by adding a solution comprising one or more of nitric acid ($HNO_3$); and hydrocarbon acid, so that the particle size in a slurry state can be decreased. Furthermore, during the firing process, air is introduced, and in this case, the $ZnFe_2O_4$ crystal structure can be relatively increased because the $Cl^-$ ions and $\alpha$-$Fe_2O_3$ crystal structure which interfere with the crystal growth are reduced.

That is, in an exemplary embodiment of the present application, the purpose is to remove $Cl^-$ ions in a solution state during the co-precipitation step, and the purpose, method and effect thereof are different from those of the introduction of an acid into the zinc ferrite-based catalyst prepared after the co-precipitation step.

In an exemplary embodiment of the present application, an amount of the acid can be 1 wt % to 30 wt %, preferably 3 wt % to 20 wt %, and more preferably 5 wt % to 15 wt %, based on a combined weight of the zinc precursor and the ferrite precursor. When the amount of the acid is less than 1 wt %, the effect of reducing $Cl^-$ ions and the $\alpha$-$Fe_2O_3$ crystal structure as described above can be negligible. Further, when the amount of the acid is more than 30 wt %, an undesired side reaction can occur because a basic material also needs to be added in excess, so that the higher amount of acid is not preferred.

In an exemplary embodiment of the present application, the solution containing the acid can comprise nitric acid ($HNO_3$) alone.

In an exemplary embodiment of the present application, the solution containing the acid can comprise hydrocarbon acid alone.

In an exemplary embodiment of the present application, the hydrocarbon acid means an acid comprising only hydrocarbon. More specifically, the hydrocarbon acid can comprise one or more of citric acid ($C_6H_8O_7$), acetic acid ($CH_3COOH$), formic acid ($CH_2O_2$), lactic acid ($C_3H_6O_3$), oxalic acid ($C_2H_2O_4$), succinic acid ($C_4H_6O_4$), and the like, but are not limited thereto.

In particular, in an exemplary embodiment of the present application, the solution containing the acid preferably comprises nitric acid or citric acid, and more preferably nitric acid.

In an exemplary embodiment of the present application, an amount of the zinc precursor can be 0.1 wt % to 5 wt % and 0.1 wt % to 3 wt %, based on a total weight of the metal precursor solution. In addition, an amount of the ferrite precursor can be 1 wt % to 10 wt % and 1 wt % to 7 wt %, based on a total weight of the metal precursor solution. When the amounts of the zinc precursor and the ferrite precursor satisfy the above-described ranges, a zinc ferrite-based catalyst is easily synthesized during the formation of a precipitate by the co-precipitation method.

In an exemplary embodiment of the present application, the zinc precursor and the ferrite precursor can be each independently one or more selected from the group consisting of nitrate, ammonium salt, sulfate, and chloride, or a hydrate thereof. Specifically, it is preferred that the zinc precursor and the ferrite precursor are nitrate or chloride, or a hydrate thereof.

In an exemplary embodiment of the present application, the zinc precursor can be zinc chloride ($ZnCl_2$). In this case, the formation of the zinc ferrite-based catalyst is excellent.

In an exemplary embodiment of the present application, the ferrite precursor can be ferric chloride hydrate ($FeCl_3 \cdot 6H_2O$). In this case, the formation of the zinc ferrite-based catalyst is excellent.

In an exemplary embodiment of the present application, as the water, pure water (DI water) and the like can be used. The temperature of the pure water (DI water) can be more than 0° C. and 40° C. or less. Preferably, the temperature can be more than 0° C. and 30° C. or less. The temperature of the water can be more preferably 5° C. to 25° C. When the temperature of the deionized water satisfies the above range, the selectivity and yield of butadiene according to the oxidative dehydrogenation reaction can be ultimately improved by increasing the amount of catalyst produced by the precipitation and adjusting the content of the active catalyst.

In an exemplary embodiment of the present application, a pH of the basic aqueous solution can be 7 to 10. Preferably, the pH can be 7.5 to 9. When the pH satisfies the above range, there is an effect of stably producing the zinc ferrite catalyst.

In an exemplary embodiment of the present application, the basic aqueous solution can be one or more selected from the group consisting of potassium hydroxide, ammonium carbonate, ammonium bicarbonate, an aqueous sodium hydroxide solution, an aqueous sodium carbonate solution, and ammonium water. Preferably, the basic aqueous solution can be ammonia water. In this case, in the process of producing a zinc ferrite-based catalyst, there is an effect that facilitates precipitation, and thus makes the formation of catalyst particles excellent.

In an exemplary embodiment of the present application, a concentration of the basic aqueous solution can be 20 wt % to 40 wt %, and 25 wt % to 30 wt %.

In an exemplary embodiment of the present application, the obtaining of the precipitate can further comprise bringing the metal precursor solution into contact with the basic aqueous solution, and then stirring the resulting solution. The formation of precipitations of metal precursors is facilitated by further comprising the stirring of the resulting solution, so that catalyst particles are favorably formed. The stirring of the resulting solution can be performed at room temperature, and the method for stirring the resulting solution can be used without limitation as long as the method mixes a liquid with a liquid. Further, the stirring time of the stirring of the resulting solution can be 30 minutes to 3 hours, and can be 1 hour to 2 hours.

In an exemplary embodiment of the present application, the filtering of the precipitate is not particularly limited as long as the method is a filtration method typically used in the art. For example, the method can be vacuum filtration. Specifically, the method can be a method of filtering the precipitate by using a vacuum pump to reduce pressure, and in this case, there are effects of washing and separating the catalyst from moisture.

In an exemplary embodiment of the present application, the method can further comprise washing the precipitate before the precipitate is filtered and then fired. Unnecessary ions remaining in the precipitate can be removed by further comprising the washing of the precipitate.

In an exemplary embodiment of the present application, the drying of the precipitate can be performed before the precipitate is fired after the precipitate is filtered and then washed. The drying of the precipitate is not particularly limited as long as the drying method is typically used in the art. For example, a dryer can be used, and an oven can be used. The drying of the precipitate can be performed at 80° C. to 150° C.

In an exemplary embodiment of the present application, the firing of the precipitate can increase temperature at 80° C. and a rate of 1° C./min and maintain the temperature at 600° C. to 800° C. for 5 hours to 10 hours. In the firing of the precipitate, the precipitate can be fired specifically at 600° C. to 700° c., and more specifically at 600° C. to 650° C. In the firing of the precipitate, the precipitate can be fired specifically for 5 hours to 8 hours, and more specifically for 5 hours to 6 hours.

The method for firing the precipitate can be a heat treatment method typically used in the art.

In an exemplary embodiment of the present application, the firing of the precipitate can be performed by injecting the air at 1 L/min into a firing furnace.

Further, another exemplary embodiment of the present application provides a zinc ferrite-based catalyst prepared by the above-described method for preparing a zinc ferrite-based catalyst.

In an exemplary embodiment of the present application, the zinc ferrite-based catalyst comprises $Cl^-$ ions, and a content of the $Cl^-$ ions can be 1,100 ppm or less, and 100 ppm to 1,100 ppm, based on a total weight of the zinc ferrite-based catalyst. When the content of the $Cl^-$ ions is more than 1,100 ppm, an excessive amount of waste water needs to be used and removed during washing. Since the Cl ions can cause corrosion of devices, it is preferred to reduce the content of the Cl ions.

In addition, an exemplary embodiment of the present application provides a method for producing butadiene, the method comprising: preparing the zinc ferrite-based catalyst; and producing butadiene by using the zinc ferrite-based catalyst in an oxidative dehydrogenation reaction of butene.

In an exemplary embodiment of the present application, the producing of the butadiene can allow a raw material comprising C4 fractions, steam, oxygen ($O_2$), and nitrogen ($N_2$) to react under the conditions of a reaction temperature of 400° C. to 600° C., a pressure condition of 0.1 bar to 10 bar, and a gas hourly space velocity (GHSV) of 100 $h^{-1}$ to 400 $h^{-1}$.

The C4 fractions can mean C4 raffinate-1,2,3 remaining by separating useful compounds from a C4 mixture produced by naphtha cracking, and can mean C4 classes which can be obtained through ethylene dimerization.

In an exemplary embodiment of the present application, the C4 fractions can be one or a mixture of two or more selected from the group consisting of n-butane, trans-2-butene, cis-2-butene, and 1-butene.

In an exemplary embodiment of the present application, the steam or nitrogen ($N_2$) is a diluted gas introduced for the purpose of reducing the explosion danger of the reactant, preventing coking of the catalyst, removing the reaction heat, and the like, in the oxidative dehydrogenation reaction.

In an exemplary embodiment of the present application, the oxygen ($O_2$) is an oxidant and reacts with C4 fractions to cause a dehydrogenation reaction.

In an exemplary embodiment of the present application, the oxidative dehydrogenation reaction can be performed according to the following Reaction Formula 1 or Reaction Formula 2.

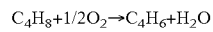  <Reaction Scheme 1>

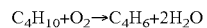  <Reaction Scheme 2>

Hydrogen of butane or butene is removed by the oxidative dehydrogenation reaction, and as a result, butadiene is produced. Meanwhile, the oxidative dehydrogenation reaction can produce a side reaction product comprising carbon monoxide (CO), carbon dioxide ($CO_2$), or the like, in addition to the main reaction such as Reaction Formula 1 or 2. The oxidative dehydrogenation reaction can comprise a process in which the side reaction product is separated so as not to be continuously accumulated in the process, and is released out of the system.

According to an exemplary embodiment of the present application, in the method for preparing butadiene, the conversion of butene can be 72% or more, preferably 72.5% or more, and more preferably 79% or more.

According to an exemplary embodiment of the present specification, in the method for producing butadiene, the selectivity of butadiene can be 85% or more, preferably 85.8% or more, and more preferably 87% or more.

FIG. 1 is an exemplary process diagram for performing a method for preparing a zinc ferrite-based catalyst according to an exemplary embodiment of the present application. Furthermore, FIG. 2 is a process diagram for performing a method for preparing a zinc ferrite-based catalyst according to the co-precipitation method in the related art.

According to FIG. 1, in the co-precipitation method of a zinc ferrite-based catalyst, it is characterized in that during the preparation of a metal precursor solution comprising a zinc precursor, a ferrite precursor, and water, a solution comprising one or more of nitric acid ($HNO_3$) and hydrocarbon acid is additionally introduced.

As described above, a zinc ferrite-based catalyst according to an exemplary embodiment of the present application can increase the size of the crystal structure of the zinc ferrite-based catalyst by introducing a solution comprising one or more of nitric acid ($HNO_3$) and hydrocarbon acid into a co-precipitation step during the process of preparing the zinc ferrite-based catalyst, and accordingly, can increase the activity of the catalyst.

Further, since the zinc ferrite-based catalyst according to an exemplary embodiment of the present application can reduce impurities $Cl^-$ ions which can be present in the catalyst, it is possible to prevent the corrosion of preparation process equipment.

Therefore, the zinc ferrite-based catalyst according to an exemplary embodiment of the present application can obtain a higher yield of 1,3-butadiene than a zinc ferrite-based catalyst in the related art, which is used for oxidative dehydrogenation of butene.

EXAMPLES

Hereinafter, the present application will be described in detail with reference to Examples for specifically describing the present application. However, the Examples according to the present application can be modified in various forms, and it is not interpreted that the scope of the present application is limited to the Examples described in detail below. The Examples of the present application are provided for more completely explaining the present application to the person with ordinary skill in the art.

Examples

<Example 1> Addition of 1 wt % of $HNO_3$

A metal precursor solution was prepared by dissolving 288.456 g of zinc chloride ($ZnCl_2$), 1132.219 g of ferric chloride (FeCl$_3$), and 23.678 g of nitric acid (HNO$_3$, 60% purity) in 2,000.00 g of pure water (DI water). In this case, the molar ratio of the metal components comprised in the metal precursor solution was Zn:Fe=1:2, and the amount of HNO$_3$ added was 1 wt % based on the combined weight of the zinc precursor and the iron precursor. An aqueous ammonia solution was added dropwise to the prepared aqueous metal precursor solution such that the pH was 7, and the resulting solution was stirred for 1 hour and co-precipitated. Thereafter, the co-precipitation solution was washed with distilled water, and dried at 90° C. for 24 hours, and then after the resulting product was warmed from 80° C. to 650° C. at a warming rate of 1° C./min under air atmosphere, a zinc-iron oxide (ZnFe$_2$O$_4$) powder having a spinel structure was produced by maintaining the temperature for 6 hours.

<Example 2> Addition of 5 wt % of HNO$_3$

A process was performed in the same manner as in Example 1, except that 5 wt % of nitric acid (HNO$_3$) was added based on the combined weight of the zinc precursor and the iron precursor.

<Example 3> Addition of 10 wt % of HNO$_3$

A process was performed in the same manner as in Example 1, except that 10 wt % of nitric acid (HNO$_3$) was added based on the combined weight of the zinc precursor and the iron precursor.

<Example 4> Addition of 10 wt % of Citric Acid (C611807)

A process was performed in the same manner as in Example 1, except that 10 wt % of citric acid (C$_6$H$_8$O$_7$) was added based on the combined weight of the zinc precursor and the iron precursor.

Comparative Example 1

A process was performed in the same manner as in Example 1 without adding nitric acid (HNO$_3$).

<Comparative Example 2> Addition of 10 wt % of Sulfuric Acid (H$_2$SO$_4$)

A process was performed in the same manner as in Example 1, except that 10 wt % of sulfuric acid (H$_2$SO$_4$) was added based on the combined weight of the zinc precursor and the iron precursor.

<Experimental Example 1> Analysis of Zinc Ferrite-Based Catalyst

A scanning electron microscope (SEM, S4800/HITACHI) analysis was performed on the zinc ferrite-based catalysts prepared in the Examples and the Comparative Examples (measured at a magnification of 180,000 times), and the results thereof are shown in the following FIGS. 3 to 6, respectively. More specifically, an SEM photograph of the zinc ferrite-based catalyst according to Example 1 is illustrated in FIG. 3, and an SEM photograph of the zinc ferrite-based catalyst according to Example 2 is illustrated in FIG. 4. Further, an SEM photograph of the zinc ferrite-based catalyst according to Example 3 is illustrated in FIG. 5, and an SEM photograph of the zinc ferrite-based catalyst according to Comparative Example 1 is illustrated in FIG. 6.

The size of the crystal structure was measured by performing the SEM analysis, and the results thereof are shown in the following Table 1. More specifically, after the surface of the sample was measured by using the SEM analysis to enlarge the surface of the sample 180,000 times, the major axis length of the crystal structures confirmed within an arbitrarily sampled range (10 μm or more in width and 15 μm or more in length) in the measured photo was measured as the size of the crystal structure. The number of measurements was at least 10 or more, and an average value of the sizes of the crystal structure obtained after the measurement was calculated.

TABLE 1

|  | Size (nm) of crystal structure |
|---|---|
| Example 1 | 750 |
| Example 2 | 900 |
| Example 3 | 750 |
| Comparative Example 1 | 550 |

From the results, it can be confirmed that when an acid solution comprising one or more of nitric acid (HNO$_3$) and hydrocarbon acid is added in the co-precipitation step during the process of preparing the zinc ferrite-based catalyst, the size of the final crystal structure of the catalyst after firing is increased. Further, it can be confirmed that when 5 wt % of nitric acid (HNO$_3$) is added in the co-precipitation step during the process of preparing the zinc ferrite-based catalyst, the final size of the crystal structure after firing is the largest.

In addition, for the zinc ferrite-based catalysts prepared in the Examples and the Comparative Examples, the content of Cl$^-$ ions in the dry powdery catalyst before the final firing was analyzed, and the results are shown in the following Table 2. Furthermore, the contents of Fe, Zn and Cl$^-$ ions in the powdery catalyst after the final firing were analyzed by inductively coupled plasma (ICP) and are shown in the following Table 3. The ICP analysis was measured by using an inductively coupled plasma-optical emission (ICP-OES) apparatus. More specifically, an ICP-OES (Optima 7300 DV) device was used, and the procedure is as follows.

1) About 0.1 g of a sample was accurately measured in a vial.
2) About 1 mL of concentrated sulfuric acid was put into the vial containing the sample.
3) The sample was carbonized by heating the sample on a hot plate.
4) The sample was allowed to react while adding a small amount of nitric acid thereto in order to promote an oxidation reaction.
5) The color of the solution was changed from dark black to light yellow by repeating the foregoing process.
6) When the sample was completely dissolved to be clear, the sample was diluted with ultrapure water so as to have a volume of 10 mL.
7) The solution was filtered and analyzed by ICP-OES.
8) ICP-OES analysis conditions
RF power (W): 1300
Torch Height (mm): 15.0
Plasma Gas Flow (L/min): 15.00
Sample Gas Flow (L/min): 0.8
Aux. Gas flow (L/min): 0.20
Pump Speed (mL/min): 1.5
Internal Standard: Y or Sc

TABLE 2

| | Cl⁻ content (wt %) |
|---|---|
| Example 1 | 3.7 |
| Example 2 | 3.0 |
| Example 3 | 3.0 |
| Comparative Example 1 | 3.7 |

TABLE 3

| | Fe (wt %) | Zn (wt %) | Cl⁻ (ppm) | Other impurities |
|---|---|---|---|---|
| Example 1 | 26.5 | 12.4 | 1004 | Not detected |
| Example 2 | 26.6 | 12.5 | 1019 | Not detected |
| Example 3 | 26.5 | 12.5 | 950 | Not detected |
| Comparative Example 1 | 26.7 | 12.5 | 1130 | Not detected |

From the results, it can be confirmed that when a solution comprising one or more of nitric acid ($HNO_3$) and hydrocarbon acid is added in the co-precipitation step during the process of preparing the zinc ferrite-based catalyst, Cl⁻ ions in the dried powdery catalyst before the final firing are reduced. Further, it can be confirmed that when an acid solution comprising one or more of nitric acid ($HNO_3$) and hydrocarbon acid is added in the co-precipitation step during the process of preparing the zinc ferrite-based catalyst, Cl⁻ ions in the powdery catalyst after the final firing are reduced.

In addition, it can be confirmed that even when a solution comprising one or more of nitric acid ($HNO_3$) and hydrocarbon acid is added in the co-precipitation step during the process of preparing the zinc ferrite-based catalyst, other impurities are not produced.

<Experimental Example 2> Analysis of Zinc Ferrite-Based Catalyst

An X-ray diffraction (XRD) analysis was performed on the zinc ferrite-based catalysts prepared in the Examples and the Comparative Examples, and the results thereof are shown in the following FIG. 8 and Table 4. In the following Table 4, the size of the $ZnFe_2O_4$ crystal structure represents the average value of the entire crystal structure.

The XRD analysis was measured by using an X-ray diffraction analyzer (Bruker AXS D4-Endeavor XRD), and performed under the analysis conditions of an applied voltage (40 kV) and an applied current (40 mA), and the range of 2 theta measured using a Cu target was 20° to 80°, and measured by performing scanning at an interval of 0.05°.

From the results of the following FIG. 8 and Table 4, according to an exemplary embodiment of the present application, the size of the fired crystal structure of the zinc ferrite-based catalyst can be increased, and accordingly, the activity of the catalyst can be increased. Further, it can be confirmed that when sulfuric acid is added as in Comparative Example 2, the formation of the $ZnFe_2O_4$ crystal is hindered.

TABLE 4

| | Size (nm) of $ZnFe_2O_4$ crystal structure |
|---|---|
| Example 3 | 120.8 |
| Example 4 | 84.5 |
| Comparative Example 2 | 24.1 |

<Experimental Example 3> Production of Butadiene

Under the conditions of 420° C., GHSV=250 $h^{-1}$, OBR=1, SBR=5, and NBR=4, 1,3-butadiene was produced from the oxidative dehydrogenation reaction by using the zinc ferrite-based catalysts prepared in the Examples and the Comparative Examples,
OBR=Oxygen/total 2-butene ratio
SBR=Steam/total 2-butene ratio
NBR=Nitrogen/total 2-butene ratio)

In addition, in the oxidative dehydrogenation reaction of butene, butene conversion, butadiene selectivity, and the like were measured, and are shown in the following Table 5.

TABLE 5

| Catalyst | Butene Conversion (%) | Butadiene Selectivity (%) | Yield (%) | COx Selectivity (%) |
|---|---|---|---|---|
| Example 2 | 67.8 | 88.4 | 59.9 | 11.6 |
| Example 3 | 65.6 | 87.7 | 57.5 | 12.2 |
| Comparative Example 1 | 65.9 | 85.1 | 56.1 | 12.0 |

From the results, it can be confirmed that when a solution comprising one or more of nitric acid ($HNO_3$) and hydrocarbon acid is added in the co-precipitation step during the process of preparing the zinc ferrite-based catalyst, the butene conversion and the butadiene selectivity are increased compared to Comparative Example 1.

In addition, even when citric acid is added as in Example 4, the effect of the increase in butene conversion and butadiene selectivity can be obtained as described above because it is possible to increase the size of the crystal structure of the zinc ferrite-based catalyst similarly to the case where nitric acid is introduced as in Examples 2 and 3. Furthermore, when sulfuric acid is added as in Comparative Example 2, the formation of the $ZnFe_2O_4$ crystal is hindered, so that the effect of the increase in butene conversion and butadiene selectivity as in an exemplary embodiment of the present application cannot be obtained.

Therefore, in an exemplary embodiment of the present application, the acid solution preferably comprises nitric acid or citric acid, and more preferably nitric acid.

As described above, a zinc ferrite-based catalyst according to an exemplary embodiment of the present application can increase the size of the crystal structure of the zinc ferrite-based catalyst by introducing an acid solution comprising one or more of nitric acid ($HNO_3$) and hydrocarbon acid into a co-precipitation step during the process of preparing the zinc ferrite-based catalyst, and accordingly, can increase the activity of the catalyst.

Further, since the zinc ferrite-based catalyst according to an exemplary embodiment of the present application can reduce impurities Cl⁻ ions which can be present in the catalyst, it is possible to prevent the corrosion of preparation process equipment.

Therefore, the zinc ferrite-based catalyst according to an exemplary embodiment of the present application can obtain a higher yield of 1,3-butadiene than a zinc ferrite-based catalyst in the related art, which is used for oxidative dehydrogenation of butene.

The invention claimed is:

1. A method for preparing a zinc ferrite-based catalyst, the method comprising:
obtaining a precipitate by bringing a metal precursor solution comprising a zinc precursor, a ferrite precursor, a solution containing an acid in an amount from 1 wt % to 30 wt % based on a combined weight of the zinc precursor and the ferrite precursor, and water into contact with a basic aqueous solution;

filtering the precipitate;

drying the filtered precipitate; and firing the dried precipitate, wherein the solution containing the acid comprises one or more of nitric acid and hydrocarbon acid, wherein the zinc ferrite-based catalyst comprises $Cl^-$ ions, and a content of the $Cl^-$ ions is 1,100 ppm or less based on a total weight of the zinc ferrite-based catalyst.

2. The method of claim 1, wherein the hydrocarbon acid comprises one or more of citric acid, acetic acid, formic acid, lactic acid, oxalic acid, and succinic acid.

3. The method of claim 1, wherein the zinc precursor and the ferrite precursor are each independently one or more selected from the group consisting of nitrate, ammonium salt, sulfate, chloride, and a hydrate thereof.

4. The method of claim 1, wherein the zinc precursor is zinc chloride.

5. The method of claim 1, wherein the ferrite precursor is ferric chloride hydrate.

6. The method of claim 1, wherein a pH of the basic aqueous solution is 7 to 10.

7. The method of claim 1, wherein the basic aqueous solution is one or more selected from the group consisting of potassium hydroxide, ammonium carbonate, ammonium bicarbonate, an aqueous sodium hydroxide solution, an aqueous sodium carbonate solution, and ammonium water.

8. The method of claim 1, wherein the zinc precursor and the ferrite precursor are the only metal precursors in the metal precursor solution.

* * * * *